(12) United States Patent
Tomita

(10) Patent No.: US 9,255,287 B2
(45) Date of Patent: Feb. 9, 2016

(54) METHOD FOR DETECTION OF CHEMICAL REACTION WITH RESPECT TO TARGET SUBSTANCE IN SAMPLE

(71) Applicant: Sharp Kabushiki Kaisha, Osaka-shi, Osaka (JP)

(72) Inventor: Naomi Tomita, Osaka (JP)

(73) Assignee: SHARP KABUSHIKI KAISHA, Osaka-shi (JP)

( * ) Notice: Subject to any disclaimer, the term of this patent is extended or adjusted under 35 U.S.C. 154(b) by 0 days.

(21) Appl. No.: 14/399,434

(22) PCT Filed: May 9, 2013

(86) PCT No.: PCT/JP2013/063039
§ 371 (c)(1),
(2) Date: Nov. 6, 2014

(87) PCT Pub. No.: WO2013/168765
PCT Pub. Date: Nov. 14, 2013

(65) Prior Publication Data
US 2015/0152472 A1 Jun. 4, 2015

(30) Foreign Application Priority Data

May 11, 2012 (JP) ................................. 2012-110043

(51) Int. Cl.
*C12Q 1/54* (2006.01)
*C12Q 1/28* (2006.01)

(52) U.S. Cl.
CPC ... *C12Q 1/54* (2013.01); *C12Q 1/28* (2013.01)

(58) Field of Classification Search
None
See application file for complete search history.

(56) References Cited

U.S. PATENT DOCUMENTS 6,121,055 A * 9/2000 Hargreaves ................... 436/526
2010/0028920 A1 2/2010 Eckhardt

FOREIGN PATENT DOCUMENTS

| JP | 10-090186 | * | 4/1998 |
| JP | 10-90186 A | | 4/1998 |
| JP | 2004-219309 A | | 8/2004 |
| JP | 2007-263812 A | | 10/2007 |
| JP | 2010-43882 A | | 2/2010 |
| JP | 2010-519935 A | | 6/2010 |
| WO | WO 89/05456 A1 | | 6/1989 |

OTHER PUBLICATIONS

Chang, H. et al. Glucose Oxidation in a Dual Hollow Fiber Bioreactor with a Silicone Tube Oxygenator. Biotechnology and Bioengineering 29:552-557, 1987.*
Dumont E. et al. Mass Transfer Coefficients of Styrene and Oxygen into Silicone Oil Emulsions in a Bubble Reactor. Chemical Engineering Science 61:5612-5619, 2006.*

* cited by examiner

*Primary Examiner* — Ralph Gitomer
(74) *Attorney, Agent, or Firm* — Birch, Stewart, Kolasch & Birch, LLP

(57) ABSTRACT

Reaction detection method to detect a chemical reaction with respect to a target substance, for instance, glucose (5) in a sample (32) includes the steps of forming a reaction layer (3) to induce the chemical reaction and forming an oxygen transfer layer (2), which has an oxygen transmission rate higher than that of the reaction layer (3) and which transfers oxygen (4) in the air (1) to the reaction layer (3), between the reaction layer (3) and the air (1), where the oxygen is consumed in the chemical reaction. Chemical reaction rate with respect to target substances in a sample is increased.

6 Claims, 5 Drawing Sheets

(a)

(b)

(c)

(d)

METHOD FOR DETECTION OF CHEMICAL REACTION WITH RESPECT TO TARGET SUBSTANCE IN SAMPLE

This application is a National Stage application filed under Rule 371 based upon PCT/JP2013/063039 filed May 9, 2013.

TECHNICAL FIELD

The present invention relates to a method for measuring the concentration of a target substance in a sample through the use of a chemical reaction, e.g., an enzyme reaction.

BACKGROUND ART

The concentration measurement of a target substance contained in a sample, e.g., a biological fluid is an analytical method widely used in medical and biochemical fields. For example, in the medical field, the measurement of glucose concentration in blood or urine is applied as an effective screening test to medical diagnoses of diseases, e.g., hypoglycemia and diabetes mellitus.

In general, a method through the use of detection of a chemical reaction with respect to a target substance in a sample is widely used as a measure to determine the concentration of the target substance at present. A method in which the sample after the reaction of the whole target substance has been completed is observed and a chemical reaction with respect to the target substance is determined on the basis of the observation is mentioned as one of such chemical reaction detection methods. However, according to this method, the waiting time until the reaction of the whole target substance in the sample is completed increases and it may be inefficient.

As for another method without being accompanied by such an inconvenience, a method in which an initial reaction rate is measured and a chemical reaction with respect to the target substance is detected on the basis of this measurement is mentioned. In this method, a sample is observed after a predetermined term is elapsed from start of the reaction of the target substance, and a total amount of reaction of the target substance at that point in time is determined. This method is effective in the case where the substrate concentration can be estimated from the reaction rate with high accuracy as with an enzyme reaction, for example, and is useful because it is not necessary to wait until the reaction of the whole target substance is completed.

Also, as for a technique used for quantitatively detecting the reaction of the target substance, a colorimetric determination method described in, for example, PTL 1 is mentioned. For example, PTL 1 describes a method in which in a saliva sugar measurement, a reduced coenzyme or hydrogen peroxide produced by using glucose oxidase-peroxidase allows other oxidation-reduction substance to take on a color and the measurement is performed with a microplate reader or a spectrophotometer.

Meanwhile, PTL 2 describes a configuration in which hydrogen peroxide assay reagents and a sample containing an analyte are combined into a droplet and the assay is conducted in the droplet to yield a detectable signal (such as color change). Also, it is disclosed that the above-described droplet may be surrounded by a filler fluid, e.g., silicon oil, that is immiscible with the droplet.

CITATION LIST

Patent Literature

PTL 1: Japanese Unexamined Patent Application Publication No. 2004-219309 (published on Aug. 5, 2004)

PTL 2: Japanese Unexamined Patent Application (Publication Translation of PCT Application) No. 2010-519935 (published on Jun. 10, 2010)

SUMMARY OF INVENTION

Technical Problem

However, as for the technology described in PTL 1, in the case where an enzyme reaction to consume oxygen exceeding the amount of dissolution in a mixture, which includes a specimen, is detected, it is necessary that oxygen be taken into the system from the outside. In the case where oxygen is taken into the system from the air directly, as described above, the oxygen uptake rate is small and, therefore, is the rate limiting step of the whole enzyme reaction. As a result, it may take a long time until the reaction of the whole target substance in the sample is completed.

Meanwhile, as for the technology described in PTL 2, the sample is combined into a droplet, so that the amount of dissolved oxygen is small in the first place. In addition, oxygen cannot be taken from the outside because the distance from the air to the sample is large and the system is substantially hermetically sealed. Consequently, it may be impossible to react the whole analyte in the sample.

The present invention has been made in consideration of the above-described problems and the present invention is to provide a reaction detection method capable of increasing a chemical reaction rate with respect to a target substance in a sample.

Solution to Problem

In order to solve the above-described issues, a reaction detection method according to the present invention is to detect a chemical reaction with respect to a target substance in a sample, the method including the steps of forming a reaction layer to induce the above-described chemical reaction and forming an oxygen transfer layer, which has an oxygen transmission rate higher than that of the above-described reaction layer and which transfers oxygen in the air to the above-described reaction layer, between the above-described reaction layer and the air, where the oxygen is consumed in the above-described chemical reaction.

According to the above-described configuration, the oxygen transfer layer having an oxygen transmission rate higher than that of the reaction layer is disposed between the reaction layer and the air. Therefore, oxygen to be consumed in the chemical reaction can be taken into the reaction layer quickly as compared with the case where the oxygen is taken from the air directly.

Consequently, the oxygen uptake rate of the reaction layer serving as the rate limiting step of the chemical reaction is increased by employing the medium of the oxygen transfer layer.

Therefore, according to the reaction detection method of the present invention, the chemical reaction rate with respect to the target substance in the sample can be increased in the reaction layer.

Also, in the reaction detection method according to the present invention, the above-described oxygen transfer layer is preferably formed by using a substance having a specific gravity smaller than the specific gravity of the above-described reaction layer.

According to the above-described configuration, in the case where each of the substances which form the reaction layer and the oxygen transfer layer is introduced in a container, the oxygen transfer layer is automatically formed as an upper layer in the vertically upward direction with respect to the reaction layer because of the difference in specific gravity between the two. Consequently, the oxygen transfer layer can be formed between the reaction layer and the air in the container without the need for a special treatment.

Also, in the reaction detection method according to the present invention, the above-described oxygen transfer layer is preferably formed by using a substance immiscible with the above-described reaction layer.

According to the above-described configuration, the oxygen transfer layer can be maintained as an independent layer without mixing with the reaction layer, so that an effect of facilitating the chemical reaction due to the oxygen transfer layer is not attenuated on the basis of, for example, a lapse of time or agitation.

Therefore, the effect of facilitating the chemical reaction due to the oxygen transfer layer can be obtained stably.

Also, in the reaction detection method according to the present invention, the above-described oxygen transfer layer is preferably formed by using silicone oil.

According to the above-described configuration, the oxygen transfer layer has a light-transmitting property and has a chemically stable property.

Consequently, the oxygen transfer layer suitable for an optical measurement of the reaction layer can be formed. In addition, denaturation of the oxygen transfer layer because of a lapse of time or agitation can be suppressed and, therefore, can be applied to various experiment systems without the need for special control.

Also, in the reaction detection method according to the present invention, the thickness of the above-described oxygen transfer layer is preferably 2 mm or less.

According to the above-described configuration, the oxygen transfer layer made from silicon oil has the above-described thickness. Therefore, oxygen can be transferred to the reaction layer efficiently, so that the chemical reaction rate can be increased reliably.

Also, in the reaction detection method according to the present invention, the above-described chemical reaction may be an enzyme reaction, and the above-described target substance may be an enzyme or a substrate.

According to the above-described configuration, an enzyme reaction with respect to a predetermined enzyme or a substrate in the sample is detected. This detection of the enzyme reaction is a technique commonly used in various biochemical analyses. Therefore, the reaction detection method according to the present invention can be utilized for various biochemical analyses.

Also, in the reaction detection method according to the present invention, the above-described target substance may be glucose.

According to the above-described configuration, the reaction detection method of the present invention can be utilized for detection of a chemical reaction with respect to glucose which is the subject of the above-described biological analysis.

Also, the reaction detection method according to the present invention may include the step of coloring the above-described reaction layer in association with the above-described chemical reaction.

According to the above-described configuration, the color of the reaction layer changes in association with the chemical reaction.

Consequently, the integrated amount of the target substance after completion of the chemical reaction can be determined at any point in time by applying light to the reaction layer exhibiting a changed color and measuring the amount of absorption of the light in the reaction layer.

Therefore, the chemical reaction with respect to the target substance can be detected by using an optical measuring method.

Advantageous Effects of Invention

As described above, the reaction detection method according to the present invention is a reaction detection method to detect a chemical reaction with respect to a target substance in a sample and the reaction detection method includes the steps of forming a reaction layer to induce the above-described chemical reaction and forming an oxygen transfer layer, which has an oxygen transmission rate higher than that of the above-described reaction layer and which transfers oxygen in the air to the above-described reaction layer, between the above-described reaction layer and the air, where the oxygen is consumed in the above-described chemical reaction.

According to the above-described configuration, the chemical reaction rate with respect to the target substance in the sample can be increased.

DESCRIPTION OF EMBODIMENTS

Figure 1:
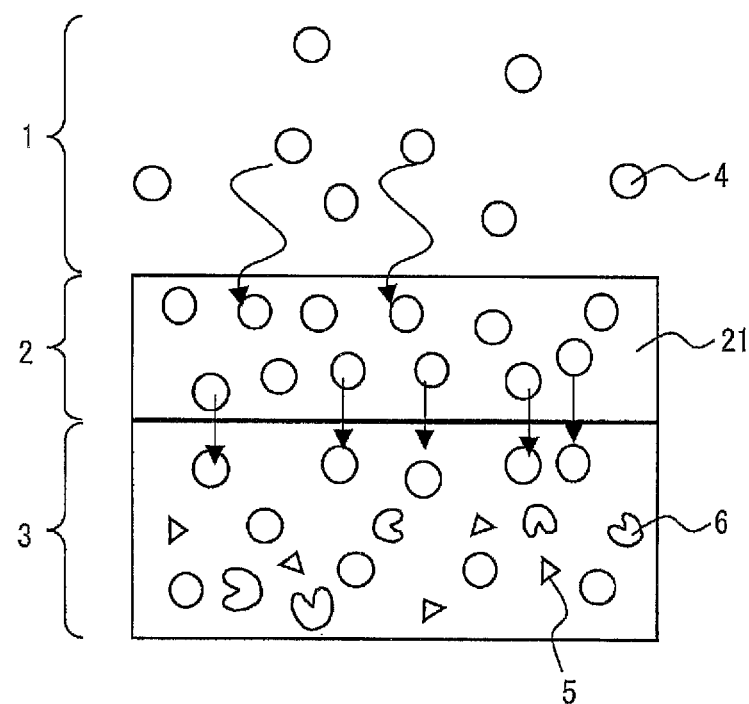
FIG. 1 is a schematic sectional view showing the manner of formation of an air layer, an oxygen transfer layer, and a reaction layer by a method according to an embodiment of the present invention.

The embodiments according to the present invention will be described below with reference to FIGS. 1 to 6. In this regard, the present invention is not limited to the following description. Meanwhile, for the convenience in explanation, the members having the same functions as those of the members shown in the individual drawings are indicated by the same reference numerals and further explanations thereof will not be provided appropriately. Also, the shapes and the dimensions, e.g., length, size, and width, of the configurations shown in the individual drawings do not reflect the actual shapes and the dimensions and are changed appropriately for the purpose of clarifying and simplifying the drawings.

To begin with, the outline of the present embodiment will be described. In the present embodiment, a reaction layer is formed by mixing a sample containing a target substance and a reaction liquid containing at least a substance which reacts with the target substance. Oxygen which is consumed by a chemical reaction in this reaction layer is taken from the air into the reaction layer sequentially. In this situation, an oxygen transfer layer to feed the oxygen from the air to the reaction layer efficiently is formed between the reaction layer and the air.

More specifically, in the present embodiment, an example in which glucose is specified to be a target substance and glucose in the sample is subjected to an enzyme reaction with glucose oxidase (GOD) in the reaction liquid will be described. In this regard, GOD may be employed as the target substance. The target substance according to the present invention is not limited to them and may be, for example, succinic acid, uric acid, glutamic oxaloacetic transaminase (AST(GOT)), glutamic pyruvic transaminase (ALT(GPT)), γ-glutamyl transpeptidase (γGTP), bilirubin, neutral fat, cholesterol, lactate dehydrogenase (LDH), and creatinine, and any substance detected through the reaction which consumes oxygen may be employed as the target substance.

Furthermore, the reaction liquid used in the present embodiment contains a coupler which takes on a color by reaction with a product of the above-described enzyme reaction, and the enzyme reaction is detected by optically measuring the reaction layer exhibiting a color changed by the coupler, so that the concentration of glucose in the sample is determined. The measuring method is not limited to the optical technique and may be, for example, an electrical measuring technique.

1. Formation Procedure of Oxygen Transfer Layer 2

The outline of formation procedure of an oxygen transfer layer 2 according to an embodiment of the present invention will be described with reference to FIG. 2 and FIG. 3.

Figure 2:
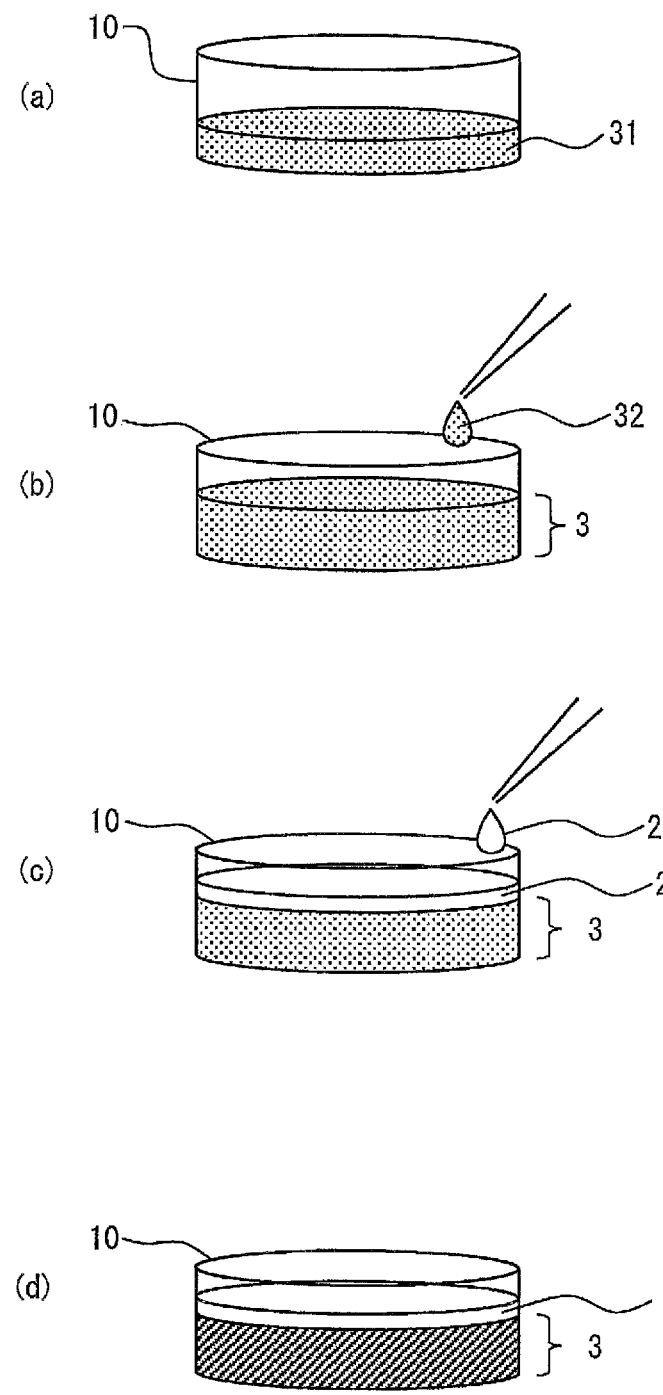
FIG. 2 shows diagrams illustrating an example of introduction procedures of the individual liquids in a method according to an embodiment of the present invention, (a) is a diagram illustrating the state in which a reaction liquid is introduced in a container, (b) is a diagram illustrating a step to further introduce a sample into the state shown in (a) and form a reaction layer, (c) is a diagram illustrating a step to further introduce silicon oil into the state shown in (b) and form an oxygen transfer layer, and (d) is a diagram illustrating the state in which the color of the above-described reaction layer has been changed by a function of a coupler in association with an enzyme reaction.

FIG. 2 shows diagrams illustrating an example of introduction procedures of the individual liquids in the present embodiment, where the oxygen transfer layer 2 is disposed between a reaction layer 3 and an air layer (the air) 1 (refer to FIG. 1) and the reaction layer 3 exhibiting a color changed in association with an enzyme reaction (chemical reaction) is measured.

In this regard, as for FIG. 2 and FIG. 3, the manner of formation of the air layer 1, the reaction layer 3, and the oxygen transfer layer 2 in a container 10 will be described. The air layer 1 is disposed in the container 10 and, therefore, the reaction layer 3 can take oxygen molecules (oxygen) 4 from the air layer 1 (refer to FIG. 1) into a reaction system.

Meanwhile, the container 10 may be, for example, a microplate, and is preferably open to the air. In the case where the container 10 is open to the air, the air layer 1 is not necessarily formed in the inside of the container 10.

FIG. 2 (a) is a diagram illustrating the state in which a reaction liquid 31 is introduced in the container 10. The reaction liquid 31 is a liquid containing at least a substance which reacts with glucose 5 serving as a target substance contained in a sample 32 and, in the present embodiment, GOD 6 (refer to FIG. 1) is contained. GOD 6 is an enzyme which catalyzes a reaction to oxidize glucose 5 to produce gluconic acid and hydrogen peroxide. The oxygen is consumed during this enzyme reaction.

Also, it is preferable that the reaction liquid 31 contain a substance to generate an indicator for detecting the reaction directly or indirectly besides GOD 6. In the present embodiment, an enzyme and a coupler (neither of them is shown in the drawing) to take on a color in association with the enzyme reaction, which generates glucose 5 and GOD 6, and color the reaction layer 3.

Specifically, the reaction liquid 31 contains peroxidase (POD) as an enzyme and 4-aminoantipyrine (4-AA) and TOOS as couplers. POD is an enzyme which catalyzes a reaction to oxidize and condense 4-AA and TOOS to generate a polymer exhibiting a peak of absorption wavelength at 555 nm. In the above-described reaction catalyzed by POD, hydrogen peroxide which is one of the products of the enzyme reaction between glucose 5 and GOD 6 is consumed. That is, when hydrogen peroxide is generated in association with the enzyme reaction between glucose 5 and GOD 6, the above-described polymer is generated by consuming this hydrogen peroxide, and the color of the reaction layer 3 is changed.

Consequently, the integrated amount of glucose 5 after completion of the reaction can be determined at any point in time of observation by, for example, applying light with a wavelength of about 555 nm to the reaction layer 3 and measuring the amount of absorption of the light. In this regard, in the present embodiment, the reaction liquid 31 is a solution in which the above-described individual substances are diluted with PBS (phosphate buffered saline).

FIG. 2 (b) is a diagram illustrating a step to further introduce a sample 32 after the state shown in FIG. 2 (a) to form the reaction layer 3. That is, the reaction layer 3 is formed by introducing the reaction liquid 31 and the sample 32 into the container 10.

In the present embodiment, the sample 32 is a PBS solution containing glucose 5 as a target substance. Glucose 5 is a substrate which induces the enzyme reaction by coming into contact with GOD 6. The reaction liquid 31 and the sample 32 are mixed and, thereby, the reaction layer 3 serving as a layer which allows glucose 5 to induce the enzyme reaction is formed. At this stage, the reaction layer 3 may be agitated to facilitate contact between glucose 5 and GOD 6.

Meanwhile, the reaction layer 3 is preferably maintained at a different temperature in accordance with the target substance. In the case where the target substance is glucose 5, the reaction layer 3 is maintained at preferably 37° C. Consequently, the enzyme reaction rate can be further increased.

FIG. 2 (c) is a diagram illustrating a step to introduce silicon oil 21 from above the reaction layer 3 formed in the state shown in FIG. 2 (b) to form the oxygen transfer layer 2.

The silicon oil 21 is immiscible with the reaction liquid 31 in PBS serving as a solvent and the sample 32 and, therefore, forms the oxygen transfer layer 2 separately from the reaction layer 3. Furthermore, the silicon oil 21 has a specific gravity smaller than the specific gravities of the reaction liquid 31 and the sample 32, so that the oxygen transfer layer 2 is formed as a layer upper than (in the vertically upward direction with respect to) the reaction layer 3. As a result, the oxygen transfer layer 2 can be formed between the reaction layer 3 and the air layer 1 without the need for a special treatment. In this regard, as a substance to form the oxygen transfer layer 2, liquid paraffin may be used in place of the silicon oil 21.

FIG. 2 (d) is a diagram illustrating the state in which the color of the reaction layer 3 has been changed by taking on a color of the coupler in association with an enzyme reaction of glucose 5. For example, the enzyme reaction between glucose 5 and GOD 6 in the reaction layer 3 can be detected by introducing the reaction layer 3 in this state into a microplate on a container 10 basis and optically measuring the reaction layer 3 in this state. Then, the concentration of glucose 5 can be measured because the enzyme reaction between glucose 5 and GOD 6 is detected.

That is, FIG. 2 (d) shows the step to color the above-described reaction layer 3 in association with the above-described enzyme reaction, and the above-described enzyme reaction in the reaction layer 3 is detected by detecting the coloring. However, the reaction detection method is not limited to the optical measurement on the basis of coloring of the reaction layer 3 but may be fluorescence detection or an optical measurement through the use of chemiluminescence. Alternatively, a current measurement in the case where an oxidation-reduction potential is given to the reaction layer 3 or an electrical measurement on the basis of an impedance measurement of the reaction layer 3 may be employed.

(Another Example of Formation Procedure of Oxygen Transfer Layer 2)

Meanwhile, the silicon oil 21 is not necessarily introduced after the reaction liquid 31 and the sample 32. Another example of formation procedure of the oxygen transfer layer 2 according to the present embodiment will be described with reference to FIG. 3.

Figure 3:
FIG. 3 shows diagrams illustrating another example of introduction procedures of the individual liquids in a method according to an embodiment of the present invention, (a) is a diagram illustrating the state in which an oxygen transfer layer has been formed in a container in advance, (b) is a diagram illustrating a step to further introduce a reaction liquid into the state shown in (a), (c) is a diagram illustrating a step to further introduce a sample into the state shown in (b) and form a reaction layer, and (d) is a diagram illustrating the state in which the color of the reaction layer has been changed by a coupler contained in the reaction liquid.
Figure 3:
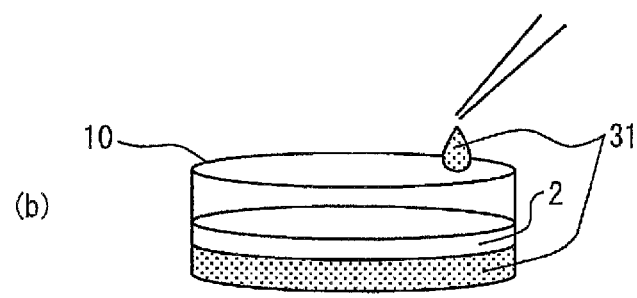
Figure 3:
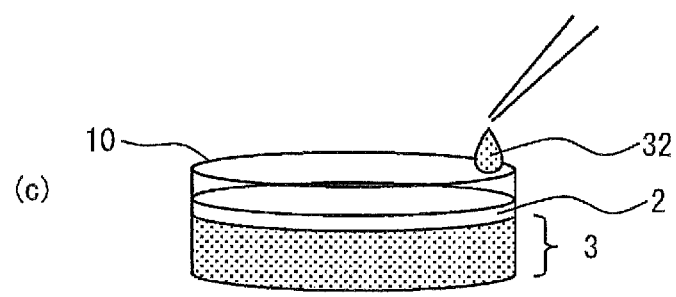
Figure 3:
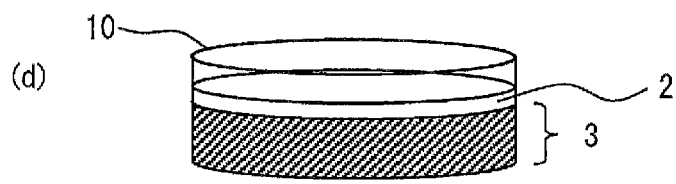

FIG. 3 (a) is a diagram illustrating the state in which the silicon oil 21 has been introduced in the container 10 in advance and, thereby, the oxygen transfer layer 2 has been formed already.

As shown in FIG. 3 (b), in the case where the reaction liquid 31 is introduced into the container 10 in the above-described state from above the oxygen transfer layer 2, the reaction liquid 31 is accumulated as a layer under the oxygen transfer layer 2 because the specific gravity of the reaction liquid 31 is larger than the specific gravity of the silicon oil 21.

Subsequently, as shown in FIG. 3 (c), when the sample 32 is introduced into the container 10 from above the oxygen transfer layer 2, the sample 32 is also moved into the layer under the oxygen transfer layer 2 because the specific gravity of the sample 32 is larger than the specific gravity of the silicon oil 21, and is mixed with the reaction liquid 31 to form the reaction layer 3. At this stage, in order to facilitate contact between the enzyme and the substrate, the reaction layer 3 may be agitated slowly in such a way that the layer structure of the reaction layer 3 and the oxygen transfer layer 2 is not disturbed.

Then, the enzyme reaction in the reaction layer 3 proceeds, and after a predetermined time is elapsed, as shown in FIG. 3 (d), the color of the reaction layer 3 is changed because of the coupler contained in the reaction liquid 31. The measurement thereafter is the same as that in the example shown in FIG. 2.

As described above, in the reaction detection method according to the present embodiment, the individual layers are formed in the container 10 in the order of the reaction layer 3 and the oxygen transfer layer 2 in FIG. 2 and in the order of the oxygen transfer layer 2 and the reaction layer 3 in FIG. 3. As described above, the silicon oil 21 constituting the oxygen transfer layer 2 is immiscible with the reaction liquid 31 and the sample 32 and has a specific gravity smaller than the specific gravities of them.

Consequently, the oxygen transfer layer 2 can be formed between the reaction layer 3 and the air layer 1 in the procedure shown in either FIG. 2 or FIG. 3. That is, the oxygen transfer layer 2 can be formed between the reaction layer 3 and the air layer 1 by introducing the above-described three types of liquids (reaction liquid 31, sample 32, and silicon oil 21) into the container 10 in any order.

Also, as shown in FIG. 2 and FIG. 3, the reaction detection method according to the present embodiment includes the step to color the reaction layer 3 in association with the enzyme reaction between glucose 5 and GOD 6. Therefore, the enzyme reaction between glucose 5 and GOD 6 can be detected by a method in which a change in color of the reaction layer 3 is optically measured, that is, by an optically measuring method.

2. Structure of Oxygen Transfer Layer

FIG. 1 is a drawing showing the oxygen transfer layer 2 according to the present embodiment together with the air layer 1 and the reaction layer 3 and is a schematic diagram illustrating the inside of the container 10 shown in FIG. 2 (c). As shown in FIG. 1, in the container 10, the reaction layer 3, the oxygen transfer layer 2, and the air layer 1 are formed in that order from the bottom of the container 10.

The air layer 1 is a gas layer containing molecules of oxygen, nitrogen, and others. In the present embodiment, the oxygen molecule 4 is a substance in the air layer 1 and is consumed by the enzyme reaction in the reaction layer 3. That is, the air layer 1 is the gas layer containing at least the oxygen molecule 4.

The oxygen transfer layer 2 is a layer to feed the oxygen molecule 4 in the air layer 1 to the reaction layer 3. The oxygen transmission rate of the oxygen transfer layer 2 is larger than the oxygen transmission rate of the reaction layer 3. In the present embodiment, the silicon oil 21 is used as a substance suitable for forming such an oxygen transfer layer 2.

The oxygen transmission rate is a quantity based on the solubility and the diffusion rate of oxygen in a certain substance and is an indicator showing the ease of transmission of oxygen in the certain substance. The oxygen transfer layer 2 has an oxygen transmission rate larger than the oxygen transmission rate of the reaction layer 3 and, therefore, can take in the oxygen molecule 4 from the air layer 1 (curved arrows in the drawing) at efficiency higher than the efficiency in the case where the reaction layer 3 takes in the oxygen molecule 4 directly from the air layer 1. In addition, the oxygen molecule 4 dissolved in the oxygen transfer layer 2 can be fed to the reaction layer 3 at high efficiency (linear arrows in the drawing).

The reaction layer 3 is a layer in which the reaction liquid 31 and the sample 32 are mixed. As described above, the enzyme reaction between GOD 6 contained in the reaction liquid 31 and glucose 5 contained in the sample 32 occurs in the reaction layer 3.

The reaction layer 3 contains the dissolved oxygen molecule 4, and at an initial stage of the above-described enzyme reaction, the above-described oxygen molecule 4 dissolved in the reaction layer 3 is consumed. However, as the above-described enzyme reaction proceeds, the oxygen molecule 4 originally dissolved in the reaction layer 3 is consumed, and in due time, the oxygen molecule 4 necessary for proceeding of the above-described enzyme reaction becomes insufficient.

Here, the reaction layer 3 is formed adjoining the oxygen transfer layer 2 and, therefore, can take in the oxygen molecule 4 dissolved in the oxygen transfer layer 2, so that the enzyme reaction can be induced at efficiency higher than the efficiency in the case where the reaction layer 3 takes in the oxygen molecule 4 directly from the air layer 1. Consequently, the enzyme reaction rate in the reaction layer 3 can be increased. Also, the inefficiency of the oxygen molecule 4 in association with proceeding of the above-described enzyme reaction can be compensated.

The mechanism for taking the oxygen molecule 4 from the air layer 1 into the reaction layer 3 through the oxygen transfer layer 2 will be specifically described below.

Usually, movement (dissolution) of the oxygen molecule 4 from a gas to a liquid is induced by collision of the oxygen molecule 4 with the liquid surface and part of the collided oxygen molecule 4 being taken into the liquid. At this time, the proportion of the collided oxygen molecule 4 taken into the liquid depends on the solubility of oxygen in the liquid. Therefore, when comparison is made between the oxygen transfer layer 2 and the reaction layer 3, where the frequencies of collision of the oxygen molecule 4 with the liquid surface are at the same level, the proportion of the collided oxygen molecule 4 taken into the liquid of the oxygen transfer layer 2 exhibiting high oxygen solubility is higher than that of the reaction layer 3.

On the other hand, movement of the oxygen molecule 4 at the interface between liquids also depends on the oxygen solubility of the liquid collided with the oxygen molecule 4 as with the above description. Here, the frequency of collision of the oxygen molecule 4 with a liquid-liquid interface is very high as compared with the frequency of collision of the oxygen molecule 4 with a gas-liquid interface (movement of the oxygen molecule 4 from the gas to the liquid). This is because the oxygen molecule 4 has high mobility of a free molecule in a gas, whereas the mobility is reduced in a liquid because of an action of an intermolecular force. Therefore, the transfer rate of the oxygen molecule 4 increases between the oxygen transfer layer 2 and the reaction layer 3, where both are liquids, as compared with the transfer rate between the air layer 1 which is a gas and the reaction layer 3 which is a liquid.

According to the above-described mechanism, the oxygen transfer layer 2 increases the gas-to-liquid movement rate of the oxygen molecule 4 serving as the rate limiting step of uptake of the oxygen molecule 4 into the reaction layer 3. Furthermore, the movement of the oxygen molecule 4 from the oxygen transfer layer 2 to the reaction layer 3 is performed smoothly because the probability of occurrence of the liquid-to-liquid movement is higher than the probability of occurrence of the gas-to-liquid movement.

Therefore, the oxygen transfer layer 2 can take in the oxygen molecule 4 from the air layer 1 at high efficiency and, in addition, can feed the resulting oxygen molecule 4 to the reaction layer 3 at high efficiency. Put another way, the oxygen uptake rate of the reaction layer 3 serving as the rate limiting step of the enzyme reaction is increased by employing the medium of the oxygen transfer layer 2.

3. Comparative Experiment: Verification of Reaction Facilitating Effect of Oxygen Transfer Layer In order to verify the effect of facilitating the enzyme reaction due to the oxygen transfer layer 2 formed in the reaction detection method according to the present embodiment, an experiment was performed to compare the enzyme reaction rate in the case where the oxygen transfer layer 2 was disposed in the container 10 and that in the case where the oxygen transfer layer 2 was not disposed.

In the present experiment, a 96-well microplate was used as the container 10, and a solution containing GOD 6 (produced by Wako Pure Chemical Industries, Ltd.) (6 U/mL), POD (produced by Wako Pure Chemical Industries, Ltd.) (2 U/mL), 4-AA (produced by Wako Pure Chemical Industries, Ltd.) (2 mM), and TOOS (produced by DOJINDO LABORATORIES) (8 mM) was used as the reaction liquid 31. A glucose solution (12 mg/dL) containing glucose 5 (produced by Wako Pure Chemical Industries, Ltd.) as a target substance was used as the sample 32. In every case, the solvent was PBS, and the total amount of the reaction liquid 31 and the sample 32 was adjusted to become 100 ml. In this regard, all the concentrations in parentheses are final concentrations. The silicon oil 21 used as the oxygen transfer layer 2 was 50 µL.

The procedure of the present experiment will be described with reference to FIG. 4.

Figure 4:
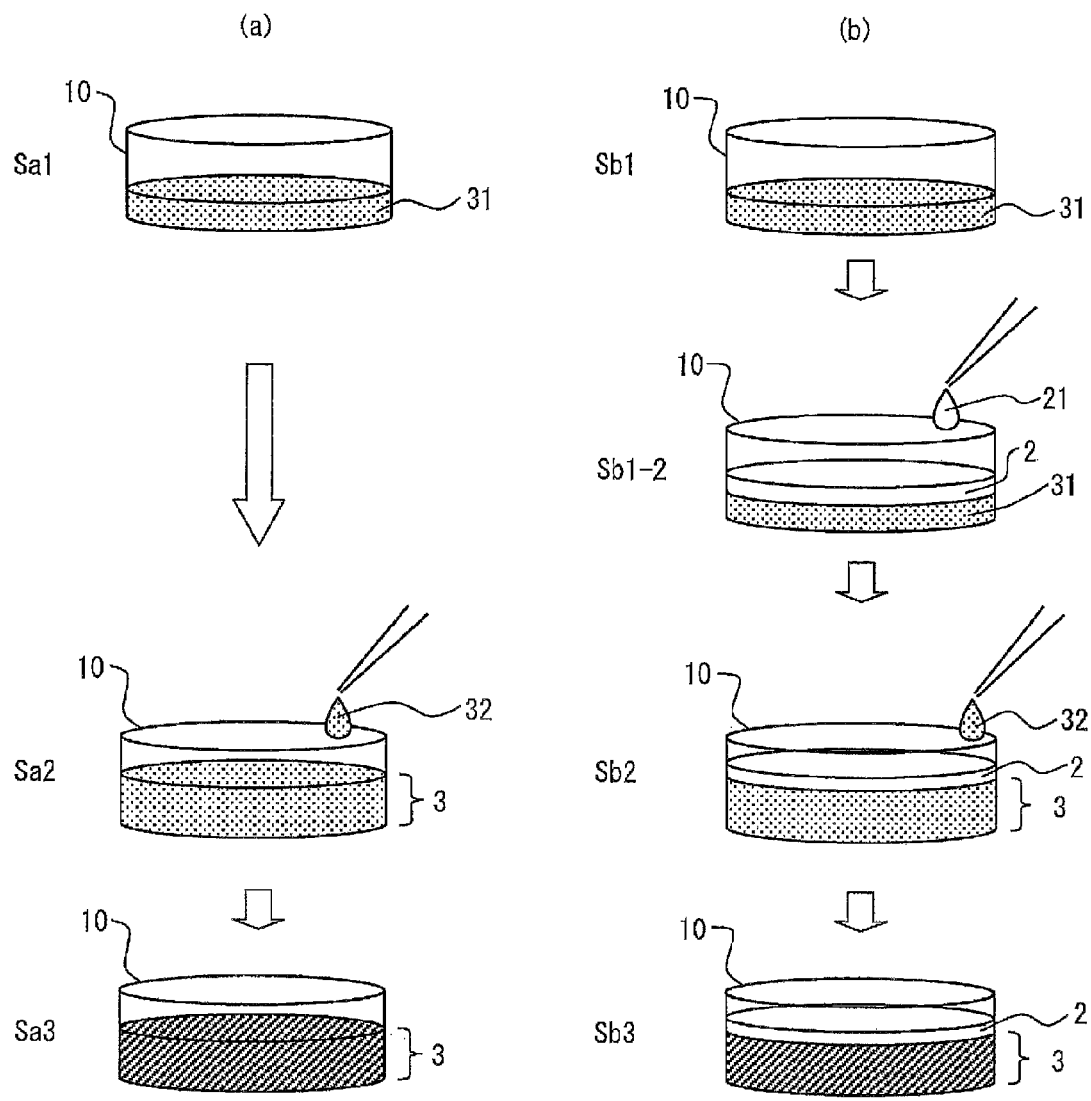
FIG. 4 shows diagrams illustrating introduction procedures of the individual liquids to perform comparative experiments for verification of the effects of the oxygen transfer layer according to an embodiment of the present invention, (a) is a diagram illustrating an introduction procedure under the condition in which an oxygen transfer layer is not disposed (Condition A) and (b) is a diagram illustrating an introduction procedure under the condition in which an oxygen transfer layer is disposed (Condition B).

FIG. 4 (a) shows diagrams illustrating an introduction procedure of the individual liquids in an enzyme reaction detection experiment under the condition in which the oxygen transfer layer 2 was not disposed (hereafter referred to as Condition A) according to a comparative example of the present embodiment.

Initially, the reaction liquid 31 containing GOD 6, POD, 4-AA, and TOOS is introduced into the container 10 (Sa1). Subsequently, the sample 32 (glucose solution) containing glucose 5 serving as the target substance is introduced (Sa2). The reaction layer 3 is formed by mixing the reaction liquid 31 and the sample 32 in the container 10. Then, after a predetermined time is elapsed, the absorbance of the reaction layer 3 exhibiting a color changed in association with the enzyme reaction between glucose 5 and GOD 6 is measured (Sa3).

FIG. 4 (b) is a diagram illustrating an introduction procedure of the individual liquids in an enzyme reaction detection experiment under the condition in which the oxygen transfer layer 2 was disposed (hereafter referred to as Condition B) according to the present embodiment. The steps of Sb1 and Sb3 are the same as Sa1 and Sa3 in Condition A and, therefore, the explanations will not be provided.

Condition B is different from the comparative example shown in FIG. 4 (a) in the point that after the reaction liquid 31 is introduced in Sb1, a step to introduce the silicon oil 21 from above the reaction liquid 31 (Sb1-2) is provided. The oxygen transfer layer 2 is formed by this introduced silicon oil 21, and the inside of the container 10 becomes the same state as the state shown in FIG. 3 (b). Subsequently, in the same manner as Sa2 shown in FIG. 4 (a), the sample 32 is introduced (Sb2). However, the sample 32 has a specific gravity larger than the specific gravity of the silicon oil 21 and, therefore, moves to a layer under the oxygen transfer layer 2, so as to be mixed with the reaction liquid 31 which has been introduced already and form the reaction layer 3. The inside of the container 10 and the movement principle of the sample 32 at this time are the same as those shown in FIG. 3 (c).

In this regard, as for Condition A and Condition B, the reaction layer 3 may be agitated between Sa2 (Sb2) and Sa3 (Sb3). However, in the case shown in FIG. 4 (b), it is necessary that the agitation be performed slowly in such a way that the layer structure of the oxygen transfer layer 2 and the reaction layer 3 is not disturbed.

Figure 5:
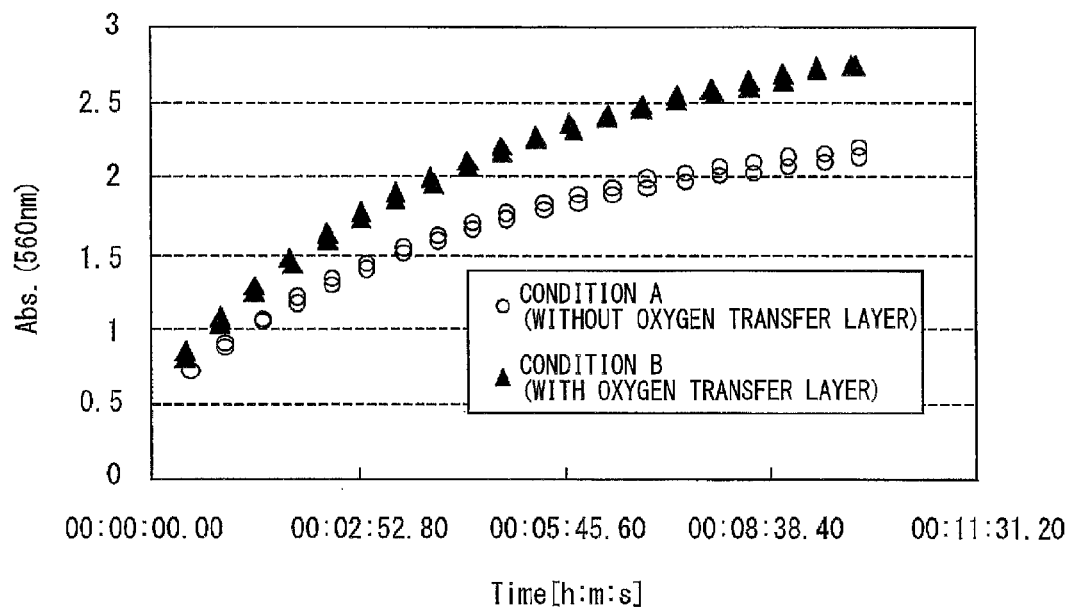
FIG. 5 is a diagram illustrating the change in absorbance of a reaction layer along with a lapse of time from the start of reaction as the results of the comparative experiments shown in FIG. 4, where the results obtained under Condition A and Condition B are shown side by side.

FIG. 5 shows the results of experiments under Condition A and Condition B. The horizontal axis of the graph indicates the elapsed time after the reaction liquid 31 and the sample 32 are mixed and the vertical axis indicates the absorbance in the case where irradiation light at 560 nm is applied to the reaction layer 3. Also, the plots indicated by circles shown in the drawing are data obtained under Condition A (without oxygen transfer layer 2) and the plots indicated by triangles are data obtained under Condition B (with oxygen transfer layer 2).

It is clear that a difference in absorbance between the two conditions is observed about 3 minutes from the start of the enzyme reaction. Also, it is clear that the time required for the absorbance to reach 2 under Condition B is reduced to about half the time under Condition A. That is, it is clear that in the case where the oxygen transfer layer 2 is not disposed, sufficient oxygen is not fed to the enzyme reaction system and, thereby, proceeding of the enzyme reaction is hindered. Thereafter, at the point in time at least 10 minutes from the start of the reaction, the absorbance under Condition A do not catch up with the absorbance under Condition B. Therefore, it is clear that the effect of increasing the enzyme reaction rate due to the oxygen transfer layer 2 under Condition B (effect of facilitating the enzyme reaction rate due to the oxygen transfer layer 2) continues.

As is shown from the above-described results, the oxygen transfer layer 2 made from the silicon oil 21 has a function of facilitating the enzyme reaction to oxidize glucose 5. That is, the enzyme reaction rate can be increased by forming the oxygen transfer layer 2 by the reaction detection method according to the present embodiment.

Here, it is considered that the oxygen molecule 4 is fed by an amount of dissolution in accordance with the thickness of the oxygen transfer layer 2 because oxygen dissolved in the oxygen transfer layer 2 is more than that in the reaction layer 3 at the start of the reaction. However, the diffusion distance of the oxygen molecule 4 increases along with an increase in thickness of the oxygen transfer layer 2, and it is feared that transfer of the oxygen molecule 4 from the air layer 1 to the reaction layer 3 is not performed efficiently. In consideration of this point, an experiment was further performed to examine an appropriate thickness of the oxygen transfer layer 2.

4. Influence of Thickness of Oxygen Transfer Layer 2

As for the amounts of the reaction liquid 31 and the sample 32 and the introduction procedure, the present experiment was performed under the same condition as Condition B in the above-described comparative experiment. However, in the present experiment, the conditions were set in such a way that the amount of the silicon oil 21 introduced in the step of Sb1-2 shown in FIG. 4 (b) was changed stepwise within the range of 0 to 300 μL, and the absorbance of the reaction layer 3 under each condition was measured.

Figure 6:
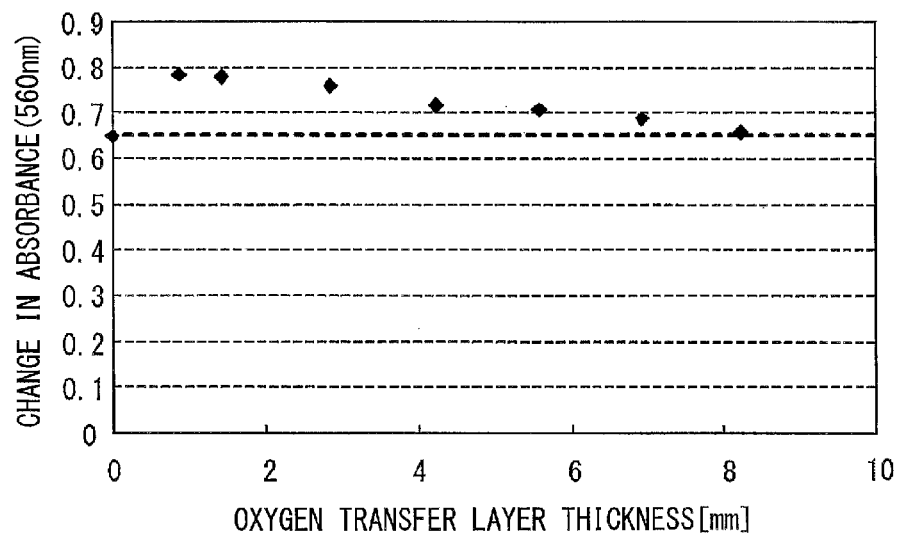
FIG. 6 is a diagram showing the correspondence relationship between the thickness of an oxygen transfer layer made from silicon oil and the amount of change in absorbance of a reaction layer at the point in time 2 minutes after the start of reaction.

The results of the present experiment are shown in FIG. 6. The horizontal axis of the graph indicates the thickness of the oxygen transfer layer 2 made from the silicon oil 21 and the vertical axis indicates the amount of change in absorbance of the reaction layer 3 at the point in time 2 minutes from the start of the reaction in comparison with the absorbance before the reaction. A broken line in the drawing indicates the numerical value of the absorbance obtained when the amount of the silicon oil 21 was 0 μL, that is, in the same procedure as that under Condition A shown in FIG. 4 (a).

As is clear from the graph shown in FIG. 6, when the thickness of the oxygen transfer layer 2 made from the silicon oil 21 is more than 0 mm and about 2 mm or less, a change in absorbance of the reaction layer 3 is at the maximum, that is, the enzyme reaction is most facilitated. On the other hand, if the above-described thickness is more than about 4 mm, the effect of facilitating the enzyme reaction is reduced and at 8 mm, the result was the same extent as the effect under Condition A in which the oxygen transfer layer 2 was not disposed.

As is clear from the above-described results, if the thickness of the oxygen transfer layer 2 increases to a certain level or more, an effect of transferring oxygen from the air layer 1 to the reaction layer 3 is impaired. Also, it can be said that in order to realize a high oxygen transfer effect due to the oxygen transfer layer 2 made from the silicon oil 21, the thickness of the oxygen transfer layer 2 is preferably more than 0 mm and 8 mm or less and in order to realize a higher oxygen transfer effect, the thickness is preferably more than 0 mm and about 2 mm or less.

Here, PTL 2 describes the example in which silicon oil is used as a filler fluid, although PTL 2 does not describe the function of the silicon oil to transfer oxygen. In addition, PTL 2 shows the configuration in which droplets are operated while being isolated from the air by the silicon oil. However, it can be said from the experiment results shown in FIG. 6 as well that the configuration does not function as the oxygen transfer layer.

5. Conclusion

As described above, in the reaction detection method according to the present embodiment, the enzyme reaction in the reaction layer 3 is detected by forming the oxygen transfer layer 2 made from the silicon oil 21 between the reaction layer 3 which induces the enzyme reaction to oxidize glucose 5 through the use of GOD 6 as a catalyst and the air layer 1 containing the oxygen molecule 4. Also, this oxygen transfer layer 2 has an oxygen transmission rate higher than that of the reaction layer 3.

Consequently, the oxygen transfer layer 2 can feed the oxygen molecule 4 in the air layer 1 to the reaction layer 3 efficiently and, thereby, the enzyme reaction in the reaction layer 3 can be facilitated. That is, according to the reaction detection method of the present embodiment, the rate of the whole enzyme reaction in the reaction layer 3 can be increased by forming the oxygen transfer layer 2.

Therefore, in the case where the concentration of the target substance in the sample 32 is determined from the observation data of the reaction layer 3 after the whole target substance has reacted, the time required until the reaction of the whole target substance is completed can be reduced.

On the other hand, in the case where the concentration of the target substance is estimated from the initial rate of the enzyme reaction, a wide range of data can be employed to determine the initial rate because the amount of dissolved oxygen in the reaction layer 3 is apparently increased by the oxygen transfer layer 2. Consequently, the accuracy of estimation of the target substance concentration on the basis of the initial rate can be improved as compared with those in PTL 1 and PTL 2, where the accuracy of detection may be lowered because of dependence on a small change in a term in which dissolved oxygen in the sample can be used.

Furthermore, the silicon oil 21 is immiscible with the reaction layer 3 and has a specific gravity smaller than the specific gravity of the reaction layer 3. Therefore, the oxygen transfer layer 2 can be formed between the air layer 1 and the reaction layer 3 easily by introducing the liquid constituting the reaction layer 3 and the silicon oil 21 into the container 10 in any order.

Meanwhile, the substrate or enzyme which induces the enzyme reaction is specified to be the target substance and, therefore, various biological analyses, e.g., inspection of vital functional disorder or infection with virus on the basis of a concentration measurement of a predetermined enzyme or substrate in the sample, can be performed. In particular, the glucose 5 is specified to be a target substance and, thereby, for example, blood sugar and urine sugar can be analyzed, so that medical diagnoses of various diseases, e.g., hypoglycemia and diabetes mellitus, can be performed.

The present invention is not limited to the above-described individual embodiments, and various modifications can be made within the scope shown in the claims. Embodiments obtained by appropriately combining the technical measures disclosed independently in the different embodiments are included in the technical scope of the present invention.

INDUSTRIAL APPLICABILITY

The present invention can be favorably utilized for analyzing biological samples in the medical field and the biochemical field.

REFERENCE SIGNS LIST 1 air layer (air)
2 oxygen transfer layer
3 reaction layer
4 oxygen molecule (oxygen)
5 glucose (target substance, substrate)
6 GOD (target substance, enzyme)
21 silicon oil
32 sample

The invention claimed is:

1. A reaction detection method to detect a chemical reaction with respect to a target substance in a sample, the method comprising the steps of:
   generating a second reaction liquid to induce the chemical reaction by mixing the sample with a first reaction liquid containing at least a substance which reacts with the target substance;
   forming an oxygen transfer layer which transfers oxygen in the air to the second reaction liquid, by introducing a substance which has an oxygen transmission rate higher than that of a substance constituting the second reaction liquid between a surface of the second reaction liquid and the air, where the oxygen is consumed in the chemical reaction, said oxygen transfer layer being formed from a substance immiscible with the second reaction liquid and being lighter in specific gravity than the second reaction liquid; and
   detecting a chemical reaction occurring in the second reaction liquid.

2. The reaction detection method according to claim 1, wherein the oxygen transfer layer is formed by using silicone oil.

3. The reaction detection method according to claim 2, wherein the thickness of the oxygen transfer layer is 2 mm or less.

4. The reaction detection method according to claim 1, wherein the chemical reaction is an enzyme reaction, and the target substance is an enzyme or a substrate.

5. The reaction detection method according to claim 4, wherein the target substance is glucose.

6. The reaction detection method according to claim 1, comprising the step of coloring the second reaction liquid in association with the chemical reaction.

* * * * *